United States Patent
Rotter et al.

(10) Patent No.: US 6,884,590 B1
(45) Date of Patent: Apr. 26, 2005

(54) METHODS OF SCREENING FOR ULCERATIVE COLITIS AND CROHN'S DISEASE

(75) Inventors: Jerome I. Rotter, Los Angeles, CA (US); Stephan R. Targan, Los Angeles, CA (US); Huiying Yang, Cerritos, CA (US); Arthur L. Beaudet, Houston, TX (US); Devendra Vora, Torrance, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/419,408

(22) Filed: Oct. 15, 1999

Related U.S. Application Data

(62) Division of application No. 08/933,824, filed on Sep. 19, 1997, now Pat. No. 6,008,335, which is a division of application No. 08/196,003, filed on Feb. 14, 1994, now Pat. No. 5,681,699.

(51) Int. Cl.[7] .............................................. G01N 33/53
(52) U.S. Cl. ............................ 435/7.1; 435/6; 435/7.2; 530/387.1; 536/23.5
(58) Field of Search ........................ 530/387.1; 435/6, 435/7.2, 7.1; 536/23.5

(56) References Cited

U.S. PATENT DOCUMENTS

| | | | |
|---|---|---|---|
| 3,654,090 A | 4/1972 | Schuurs | 195/103.5 |
| 3,850,752 A | 11/1974 | Schuurs et al. | 195/103.5 |
| 4,016,043 A | 4/1977 | Schuurrs et al. | 195/103 |
| 4,698,195 A | 10/1987 | Okumura et al. | 264/235.6 |
| 4,699,880 A | 10/1987 | Goldstein | 435/172.2 |
| 4,704,692 A | 11/1987 | Ladner | 364/496 |
| 4,800,159 A | 1/1989 | Mullis et al. | 435/172.3 |
| 4,935,234 A | 6/1990 | Todd et al. | 424/85.8 |
| 5,002,873 A | 3/1991 | St. John et al. | 435/69.1 |
| 5,085,318 A | 2/1992 | Leverick | 206/312 |
| 5,091,302 A | 2/1992 | Newman et al. | 435/6 |
| 5,114,842 A | 5/1992 | Plow et al. | 424/85.8 |
| 5,137,806 A | 8/1992 | Lemaistre et al. | 435/6 |
| 5,147,637 A | 9/1992 | Wright et al. | 424/85.8 |
| 5,219,997 A | 6/1993 | Schlossman et al. | 530/388.7 |
| 5,227,369 A | 7/1993 | Rosen et al. | 514/23 |
| 5,234,810 A | 8/1993 | Kehrli, Jr. et al. | 435/6 |
| 5,235,049 A | 8/1993 | McClelland et al. | 435/240.2 |
| 5,236,554 A | 8/1993 | Fitzsimmons et al. | 206/44 |
| 5,264,554 A | 11/1993 | Newman | 530/387.1 |
| 5,272,263 A | 12/1993 | Hession et al. | 536/23.5 |
| 5,284,931 A | * 2/1994 | Springer et al. | 424/85.8 |
| 5,518,488 A | 5/1996 | Schluger | 493/82 |
| 5,590,769 A | 1/1997 | Lin | 206/308.1 |
| 5,947,281 A | 9/1999 | Kaneff | 206/313 |

FOREIGN PATENT DOCUMENTS

| | | |
|---|---|---|
| WO | 9116928 | 4/1991 |
| WO | 9202819 | 7/1991 |
| WO | 9222323 | 6/1992 |
| WO | 9312248 | 12/1992 |
| WO | 9404188 | 8/1993 |

OTHER PUBLICATIONS

Stratagene Catalog, 1988, p. 39.*
Paul, ed. Fundamental Immunology 4th edition 1998 pp. 663–665.*
Ausubel, F. M. et al., eds., "Current Protocols in Molecular Biology," Wiley Intersciences, New York, (1987, 1989).
Ballantyne, C., et al., "Short Communication, Assignment of the Gene for Intercellular Adhesion Molecule–1 (Icam–1) to Proximal Mouse Chromosome 9," *Genomics* —9:547–550 (1991).
Benoit, R., et al., "Presence of somatostatin–28–(1–12) in hypothalamus and pancreas," *Proc. Natl. Acad. Sci. USA*— 79:917–921 (1982).
Brambs et al., "Inflammatory Bowel Disease: Radiographical Diagnostics." (Reprints available at the Department of Radiography, Albert Ludwigs University Hospital, Freiburg, Federal Republic of Germany),. pp. 3–62 (Undated).
Burks, C., et al., "GenBank," *Nucleic Acids Res. (Suppl.)*— 20:2065–2069 (1992).
Cardullo, R.A., et al., "Detection of nucleic acid hybridization by nonradiative fluorescence resonance energy transfer," *Proc. Natl. Acad. Sci. USA*—85:8790–94 (1988).
Diamond, M.S., et al., "Binding of the Integrin Mac–1 (CD11b/CD18) to the Third Immunoglobulin–like Domain of ICAM–1 (CD54) and its Regulation by Glycosylation," *Cell*—65(6):961–971 (1991).
Fawcett, J., et al., "Molecular cloning of ICAM–3, a third ligand for LFA–1, constitutively expressed on resting leukycytes," *Nature*—360:481–84 (1992).
Hogg, N. and Landis, R., "Adhesion molecules in cell interactions," *Curr. Opin. Immunol.*—5:383–390 (1993).
Kita, Y., et al., "Sequence and expression of rat ICAM–1," *Biochim. Biophys. Acta*—1131:108–111 (1992).
Kuntz, H.D., et al., "Inflammatory Bowel Disease: Endoscopic Diagnostics." (Reprints available at the Department of Gastroenterology and Hepatology "Bergmannsheil" Hospital, University of Bochum, Federal Republic of Germany), pp. 3–38 (Undated).
Landegren, U., et al., "A Ligase–Mediated Gene Detection Technique," *Science*—241:1077–80 (1988).
Lasky, L., "Selectins: Interpreters of Cell–Specific Carbohydrate Information During Inflammation," *Science*— 258:964–969 (1992).

(Continued)

Primary Examiner—Yvonne Eyler
Assistant Examiner—Joseph S. Murphy
(74) Attorney, Agent, or Firm—McDermott, Will & Emery

(57) ABSTRACT

A novel association between IBD and a polymorphism at amino acid residue 241 of ICAM-1 has been discovered. In accordance with the present invention there is provided methods of screening for IBD, methods for treating IBD, antibodies specifically reactive with ICAM-1 encoded by, R241 allele and kits which exploit the inventive methods.

23 Claims, No Drawings

OTHER PUBLICATIONS

Lemna, W.K., et al., "Mutation Analysis for Heterozygote Detection and the Prenatal Diagnosis of Cystic Fibrosis," *N. Eng. J. Med.—322*:291–296 (1990).

Lipsky, P., "Structure, Function and Regulation of Molecules Involved in Leukocyte Adhesion," New York: Springer–Verlag (1993) (Book–not being sent).

Lorenz–Meyer, H., "Inflammatory Bowel Disease Laboratory Diagnostics." (Reprints available from the City Hospital, Friedrichshafen, Federal Republic of Germany), pp. 3–29 (Undated).

Maniatis, T. et al., Molecular Cloning: A Laboratory Manual, Cold Spring Harbor Laboratory Press, pp. (1982).

McEver, R., "Leukocyte—endothelial cell interactions," *Curr. Opin. Cell. Biol.—4*:840–849 (1992).

Nakamura, S., et al., "In situ expression of the cell adhesion molecules in inflammatory bowel disease: Evidence of immunologic activation of vascular endothelial cells," *Lab Invest.—69*(1):77–85 (1993).

Saxon, E.Z., et al., "A Distinct Subset of Antineutrophil Cytoplasmic Antibodies is Associated with Inflammatory Bowel Disease," *J. Allergy Clin. Immunol.—86*(2):202–210 (1990).

Schoelmerich, J., "Inflammatory Bowel Diseases: Early Symptoms and Differential Diagnosis of Chronic Inflammatory Bowel Diseases," (Reprints available from the University of Freiburg, Department of Internal Medicine, Hugstetter Straβe 55, D–7800 Freiburg, W. Germany), pp. 2–20.

Shanahan, F., et al., "Inflammatory Bowel Disease," *Textbook of Internal Medicien—81*:489–502; (W.N. Kelley et al. (editor), 2$^{nd}$ edition, J. B. Lippincott Company, Philadelphia, PA (1992).

Smith, C., "Transendothelail Migration," Harlan, J. and Liu, D., eds., W.H. Freeman & Co., New York, pp. 83–115 (1992).

Smith, C., et al., "Adherence of Neutrophils to Canine Cardiac Myocytes In Vitro Is Dependent on Intercellular Adhesion Molecule–1," *J. Clin. Invest.—88*:1216–1223 (1991).

Smith, C.W., et al., "Recognition of an Endothelial Determinant for CD18–dependent Human Neutrophil Adherence and Transendothelial Migration," *J. Clin. Invest.— 82*:1746–1756 (1988).

Springer, T.A., et al., "Leukocyte Adhesion Molecules Structure Function and Regulation," New York, Springer–Velag (1990) (Book—Table of Contents).

Springer, T.A., et al., "Adhesion receptors of the immune system," *Nature—346*:425–433 (1990).

Staunton D.E., et al., "Primary Structure of ICAM–1 Demonstrates Interaction Between Members of the Immunoglobulin and Integrin Supergene Families," *Cell—52*:925–933 (1988).

Stites, D. P., et al., Chapter 22 of the 4$^{th}$ edition of *Basic and Clinical Immunology*, Lange Medical Publications, Los Altos, California (1982).

Tomassini, J.E., et al., "cDNA Cloning Reveals That The Major Group Rhinovirus Receptor on HeLa Cells is Intercellular Adhesion Molecule 1,"*Proc. Natl. Acad. Sci. USA— 86*:4907–4911 (1989).

Voraberger, G., et al., "Cloning of the Human Gene For Intercellular Adhesion Molecule 1 and Analysis of Its 5'–Regulatory Region," *The Journal of Immunology— 147*:(8):2777–2786 (1991).

Weber, J. and May, P., "Abundant Class of Human DNA Polymorphisms Which Can Be Typed Using the Polymerase Chain Reaction," *Am. J. Hum. Genet.—44*:388–396 (1989).

Yang, H. et al., "Association of intercellular adhesion–molecule–1 (ICAM–1) gene with subsets of Inflammatory bowel disease (BID) stratified by anti neutrohil cytoplasmic antibodies (ANCAs)," *Clinical Research—42*(1):76A (1994).

Yang, H., et al., "Genetic Heterogeneity Within UC and Crohn's Defined by Antineutrophil Cytoplasmic Antibodies (ANCAs) and Intercellular Adhesion Molecule–1 (ICAM–1) Polymorphisms," *Gastroenterology 106*(4) Part 2 (A794–AGA Abstracts).

\* cited by examiner

METHODS OF SCREENING FOR ULCERATIVE COLITIS AND CROHN'S DISEASE

This application is a divisional of application Ser. No. 08/933,824, filed Sep. 19, 1997 now U.S. Pat. No. 6,008,335, which is a divisional of application Ser. No. 08/196,003, filed Feb. 14, 1994, now U.S. Pat. No. 5,681,699.

I. ACKNOWLEDGEMENT

This invention was made with Government support under grants DK43026, DK46763, awarded by the National Institute of Health. The Government has certain rights in this invention.

II. FIELD OF THE INVENTION

The present invention relates to cellular adhesion molecules. More specifically, this invention relates to a genetic polymorphism in intercellular adhesion molecule-1 ("ICAM-1") which has been found to be associated with ulcerative colitis and Crohn's disease.

III. BACKGROUND OF THE INVENTION

A. Inflammatory Bowel Disease

Inflammatory Bowel Disease ("IBD") is the collective term used to describe two chronic, idiopathic inflammatory diseases of the gastrointestinal tract: ulcerative colitis ("UC") and Crohn's disease ("CD"). UC and CD are considered together because of their overlapping clinical, etiologic, and pathogenetic features. From a therapeutic and prognostic standpoint, however, it is important to distinguish them.

IBD occurs world-wide and is reported to afflict as many as two million people. Onset has been documented at all ages; however, IBD predominately begins in young adulthood. The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD. Reports of an increasing occurrence of psychological problems, including anxiety and depression, are perhaps not surprising secondary effects of what is often a debilitating disease that occurs in people in the prime of life.

B. Methods of Diagnosing IBD

A battery of laboratory, radiological, and endoscopic evaluations are combined to derive a diagnosis of IBD and to assess the extent and severity of the disease. Nevertheless, differentiating UC from CD, as well as other types of inflammatory conditions of the intestines, such as irritable bowel syndrome, infectious diarrhea, rectal bleeding, radiation colitis, and the like, is difficult, because the mucosa of the small and large intestines reacts in a similar way to a large number of different insults. Once other types of bowel disorders have been ruled out, the final diagnosis is often made on the basis of the progression of the disease. In many patients, though, the colitis must still be regarded as indeterminate because of the overlapping features of UC and CD, particularly with CD of the colon.

1. Early Symptoms of IBD

The leading early symptoms of UC and CD are chronic recurrent diarrhea, bloody diarrhea, recurrent abdominal pain, nausea, weight loss general evidence of inflammation without any obviou's explanation (fever, raised ESR, leucocytosis, thrombocytosis and dysproteinenemia or anemia). Among these symptoms, diarrhea and anemia are more characteristic of UC while pain and weight loss and marked evidence of inflammation are more common in CD. While the history and physical examination of a patient can help, the final confirmation of the diagnosis has traditionally been made endoscopically, histologically and, in relation to the small intestine, radiologically as well.

2. Endoscopic and/or Radiologic Examination

An endoscopic examination of the bowel can reveal important changes in mucosal appearances which can aid the physician in diagnosing IBD.

Unlike CD, UC is a disease of the mucosa and is confined to the large intestine. UC usually begins in the rectum, although it may involve the entire colon at the time of presentation. When UC spreads, it spreads proximally and continuously, without skipping areas. Hence, it is important to take multiple biopsy specimens from different sites of involved and apparent uninvolved mucosa. In some patients, UC remains localized to the rectum or to the left side of the colon.

The mucosa in acutely active UC appears to be hyperemic, granular and friable, while CD shows lymphoid follicles, aphthoid lesions and flat ulcers. Despite its name, inflammation rather than ulceration is the cardinal feature of UC. Ulcerations may or may not be present in UC. Occasionally, inflammation and ulceration vary in severity in different parts of the colon, including the rectum, giving the false impression of skip areas and rectal sparing, the latter of which are features of CD and are of diagnostic importance for that disorder.

The mucosa of CD exhibits patchy involvement with edema, hyperemia, and ulcerations. The ulceration is a prominent feature of CD. Both superficial and deep undermining or cleft-like ulcers occur. They may be linear or serpiginous. Occasionally, the combination of edema with ulcerations creates a cobblestone appearance that is seen radiologically and endoscopically. Inflammatory polyps, as in UC, may occur.

3. Histological Examination

The cardinal histological features in UC include vascular congestion, edema, goblet cell mucin depletion, crypt abscess formation, and inflammatory cell infiltration of the lamina propria. Crypt abscesses are collections of neutrophils that invade the crypt epithelium and accumulate within the lumen of the crypts. Ulcerations, if they occur, are superficial and only become penetrating to the propria muscularis when the disease is fulminant and acute toxic dilatation of the colon occurs.

Histology in CD shows the characteristic findings of granuloma formation with epithelioid and giant cells. However, these features are found in only 20–40% of biopsies. Transmural inflammation is also typical of CD, and even more typical is its disproportionate distribution (submucosa>mucosa). The mucosa shows infiltration by granulocytes with preservation of normal numbers of goblet cells. Lymphocytes and plasma cells are found in the lamina propria, and lymphoid aggregates are present. Lastly, aphthoid lesions ate a typical histological feature in the early stages.

4. Determination of ANCA Status

The presence of anti-neutrophil cytoplasmic antibodies ("ANCAs") can easily be detected in a blood sample, for example, by immunofluorescence assay or a fixed neutrophil ELISA as detailed in Saxon, et al., *J. Allergy Clin. Immunol.*

Vol. 86 No. 2, pp. 202–210 (1990) and incorporated herein by reference. The prevalence of positive ANCA in patients with UC ranges from 50 to 86%. This UC-associated ANCA has perinuclear immunofluorescence binding pattern which is different from other ANCAS. Moreover, the presence of ANCA is highly specific for UC compared with other forms of colitis. Although a proportion of CD exhibit ANCA, it is at a much lower titre than UC.

Thus the ANCA status of a patient (positive indicating UC and negative indicating CD) is another factor that aids the physician in the diagnosis of IBD. ANCAs also have an increased frequency: among the clinically healthy relatives of UC patients compared with environmental and ethnically matched controls. Therefore, ANCA status, in combination with family history of IBD, has also aided physicians in predicting a subjects susceptibility to IBD.

To date, a diagnosis of UC or CD is quite subjective and depends upon host of procedures aimed at confirming the suspected diagnosis. The initial symptoms are often confused for non-chronic bowel disorders by physicians unfamiliar with IBD. Consequently, IBD is often goes mistreated and undiagnosed until the disease shows its chronicity which results in referral of the patient to a specialist. The imprecise and subjective nature of endoscopic and radiologic examination can result in a misdiagnosis between UC and CD or indeterminate diagnosis even when the IBD is suspected.

Histological examination and ANCA status do provide greater certainty of an accurate diagnosis, but the problems of differentiating between the two diseases based on the histological findings are often underestimated. There is no single histological criterion which is proof of one or the other disease. The epithelial cell granuloma for example, which is often accorded a key role in the diagnosis of CD is only to be found in about 20% of bioptic specimens from such patients. They can also occur in other diseases. Unfortunately, the patient must often suffer as the disease progresses before a definitive diagnosis can be made.

The selective identification of UC as opposed to CD or other inflammatory conditions of the intestines carries important prognostic and therapeutic implications. For example, when colectomy is indicated, the type of IBD involved determines which surgical options are appropriate. Surgery (total colectomy) does represent a cure in UC, though a dramatic one. In CD, surgery is never curative. Continent procedures such as the ileorectal pull-through (mucosal proctectomy) or the Kock pouch may be desirable in UC, but are contraindicated in CD.

C. Inflammation and Intercellular Adhesion Molecules

Although the cause(s) of UC and CD is not known, there is general agreement that genetics is important in a person's susceptibility to UC and CD and that the immune system is responsible for mediating the tissue damage in these diseases. A wide range of immunologic abnormalities have been reported in these disorders, but none has yet been sufficiently reliable to be of diagnostic value.

What characterizes the various forms of IBD is a failure to down regulate the normal self-limited inflammatory response of the gut. Inflammation is the response of vascularized tissue to infection or injury. Clinically it is accompanied by four classic signs: redness, heat, pain and swelling. Its course may be acute or chronic.

At the cellular level, inflammation involves the adhesion of leukocytes (white blood cells) to the endothelial wall of blood vessels and their infiltration into the surrounding tissues. In normal inflammation, the infiltrating leukocytes phagocytize invading organisms or dead cells, and play a role in tissue repair and the immune response. However, in pathologic inflammation, infiltrating leukocytes can cause serious and sometimes deadly damage.

Recognizing that leukocyte infiltration is the cause of much inflammation-related pathology and that leukocyte dhesion is the first step in infiltration, investigators have recently focused attention on the mechanism of leukocyte binding to the endothelium cell surface. Studies show that binding is mediated by cell-surface molecules on both endothelial cell and leukocytes, which act as receptor and ligand. For a review of the roles of leukocyte integrins, immunoglobulin (Ig) gene family members, and selections in the leukocyte rolling, attachment, and transendothelial migration, the reader is directed to Springer, T. A., et al., Nature, 346: 425–433 (1990); Springer, T. A., et al., "Leukocyte Adhesion Molecules Structure Function and Regulation," New York: Springer-Velag (1990); Lasky, L. A., Science 258: 964–969 (1992); McEver, R. P., Curr. Opin. Cell. Biol. 4: 840–849 (1992); Lipsky, P. E., "Structure, Function and Regulation of Molecules Involved n Leukocyte Adhesion," New York: Springer-Verlag (1993); Hogg, N. and Landis, R. C., Curr. Opin. Immunol. 5: 383–390 (1993), all of which are incorporated herein by reference.

Transendothelial migration begins with leukocyte rolling which is largely brought about by the selections Lasky, et al., 1992. The later stages of endothelial migration involve activation of leukocyte integrins and binding of leukocytes to the endothelial cells which express Ig-like proteins including intercellular adhesion molecule-1 ("ICAM-1"). The interaction of leukocyte integrins with the Ig-like proteins leads to firm attachment and actual migration across the endothelial surface (see, Smith, C. W., et al., J. Clin. Invest. 82: 1746–1756 (1988) and Smith, C. W., "Transenothelial Migration." ed. Harlan, J. M. and Liu, D. Y. New York: W. H. Freeman & Co. pp. 83–115 (1992), incorporated herein by reference). Thus, a genetic variation in these inflammatory cell adhesion molecules would be an important variable in the susceptibility, diagnosis and treatment of multifactorial disease processes like IBD which involve inflammatory or immunological responses.

The availability of a diagnostic marker that would readily distinguish UC from CD of the colon, independent of or in combination with existing diagnostic methods, would represent a major clinical advance which would aid in therapeutic management of IBD and the design of more specific treatment, modalities. Accordingly, there has existed a need for a convenient and reliable method to distinguish UC from CD for diagnostic, prognostic and therapeutic purposes.

IV. BRIEF DESCRIPTION OF THE INVENTION

A novel association between Inflammatory Bowel Disease ("IBD") a polymorphism in intercellular adhesion molecule-1 ("ICAM-1") has been discovered. In accordance with the present invention there is provided methods of screening for IBD, comprising assaying nucleic acid of a subject for the presence or absence of R241 allele of the ICAM-1 gene, wherein the presence of said R241 allele is indicative of IBD.

Also provided are novel antibodies specifically reactive with ICAM-1 encoded by R241 allele of the ICAM-1 gene. In addition, methods of screening for IBD, comprising assaying a tissue sample from a subject for the presence or absence of arginine at amino acid residue 241 of ICAM-1 wherein the presence of arginine at amino acid residue 241 of ICAM-1 is indicative of IBD.

Therapeutic methods for treating IBD and kits for exploiting the inventive methods of the present invention are also provided.

V. DETAILED DESCRIPTION OF THE INVENTION

An association between IBD and a polymorphism in ICAM-1 has been discovered. This polymorphism provides the basis for convenient and reliable methods of screening for IBD, providing physicians with valuable information in the diagnosis of IBD and the determination of susceptibility to IBD. This polymorphism can also be exploited in therapeutic treatments of IBD.

Unless defined otherwise, all technical and scientific terms used herein have the same meaning as is commonly understood by one of: skill in the art to which this invention belongs. All U.S. patents and all publications mentioned herein are incorporated in their entirety by reference thereto.

The amino acids, which occur in various amino acid sequences appearing herein, are identified according to their well-known, three letter or one letter abbreviations. The nucleotides, which occur in the various nucleic acid sequences described herein, are designated with the standard single-letter designations used routinely in the art.

The gene structure for human ICAM-1 was characterized in Voraberger, et. al., *J. Immunol.* 147: 2777–86 (1991) (incorporated herein by reference) and the gene was localized to chromosome 19 as reported in Greve, J. M., et al., *Cell* 56: 839–847 (1989) (incorporated herein by reference). The ICAM-1 gene was found to be distributed over seven exons separated by six introns. The five extracellular Ig-like domains of ICAM-1 gene are each encoded by its own exon. A representative genomic DNA sequence of exon 3, intron 3, exon 4, intron 4 and exon 5 (in consecutive order reading 5' to 3') for human ICAM-1 is set forth in SEQ ID NO 1. The complete nucleotide sequence of the ICAM-1 gene is published in EMBL GenBank database under accession numbers X59286, X59287 and X59288, all of which is incorporated herein by reference.

The polymorphism of ICAM-1 found to be associated with IBD is located in exon 4 of the human ICAM-1 gene, wherein the codon corresponding to amino acid 241 of ICAM-1 may encode Gly (e.g., GGG, GGA, GGC, GGT) or Arg (e.g., AGG, AGA, CGT, CGC, etc.). Thus, the polymorphism is referred to herein as "G/R 241." A nucleic acid encoding a glycine at amino acid residue 241 of ICAM-1 is referred to herein as the "G241 allele" or the "G241 allele of the ICAM-1 gene." A nucleic acid encoding an arginine at amino acid residue 241 of ICAM-1 is referred to herein as the "R241 allele" or the "R241 allele of the ICAM-1 gene." The term "codon 241" as used herein refers to a codon in a nucleic acid sequence which encodes amino acid residue 241 of ICAM-1.

A detailed description of the experimental methods used to discover the association of the G/R 241 polymorphism with IBD is provided in the "Examples" set forth below. A total of 118 UC patients and 127 CD patients from the clinical IBD programs at Cedars-Sinai Medical Center and the University of California, Los Angeles were involved. The study protocols were approved by each institution's Human Subject Review Committee. The diagnosis of UC was documented by conventional endoscopic, histological, and clinical criteria. The UC patients studied did not have multiple sclerosis, systemic lupus erythematosus, or other recognized autoimmune diseases.

To select an ethnically, socioeconomically matched control group for the association study, 71 controls were ascertained from the spouses or acquaintances of the patients. An individual was used as control only if he/she did not have inflammatory bowel disease, multiple sclerosis, systemic lupus erythematosus, or other recognized autoimmune diseases. The distribution of age, gender, and ethnicity (Jewish/non-Jewish) were comparable between patients and controls. All patients and controls analyzed are Caucasians.

Briefly stated, genomic DNA from test subjects and control subjects was isolated and a region encoding amino acid 241 of ICAM-1 was amplified. Each subject's DNA was tested using allele-specific oligonucleotide probes to determine which of the two allele (G241 or R241) was encoded. The ANCA status (positive or negative) of each subject was determined using fixed-neutrophil ELISA. Positive ANCA status was confirmed by indirect immunofluorescence.

It was determined that the R241 allele is the less frequent allele at codon 241 as compared with the G241 allele. Table 1 shows the homozygous and heterozygous allele occurrence and the allele frequency for UC, CD and control subjects. The R241 allele frequency was 8.0% in patients with UC (considered as one group), 10.2% in patients with CD (taken as one group), and 6.4% in our ethnically matched control group. The difference between any two of the groups is not statistically significant.

TABLE 1

Comparison between UC or CD and Controls

|  |  | Genotype (%) | | | Allele (%) | |
|---|---|---|---|---|---|---|
| G/R241 | N | GG | GR | RR | G | R |
| UC | 117 | 85.5 | 12.8 | 1.7 | 92.0 | 8.0+ |
| CD | 127 | 81.1 | 17.3 | 1.6 | 89.8 | 10.2+ |
| Control | 70 | 87.1 | 12.9 | 0.0 | 93.6 | 6.4 |

+comparisons with control group are not statistically significant

However, when UC and CD patients were divided into subgroups depending on the presence or absence of ANCA, a significant difference was observed between ANCA(+) UC and ANCA(−) UC, and between ANCA(+) CD and ANCA(−) CD in the frequencies of the codon 241 polymorphism. As shown in Table 2, ANCA(−) UC exhibited a statistically significant increase of R241 allele compared to the ANCA(+) UC (16.0% vs. 5.6%, p=0.016). ANCA(+) CD had a similar statistically significant increase compared to ANCA(−) CD (20.4% vs. 8.3%, p=0.014). The remaining groups, i.e., ANCA(+) UC and ANCA(−) CD, have a similar frequency of the polymorphism to controls (5.6% in ANCA(+) UC, 8.3% in ANCA(−) CD, and 6.4% in controls). The significance of any associations of ICAM-1 alleles with UC or CD each taken as one group, or with subsets of UC or CD stratified by ANCAs, was tested using a chi-square test or Fisher's exact probability test when appropriate.

TABLE 2

Comparisons within UC and within CD as a function of ANCA Status

|  |  | Genotype (%) | | | Allele (%) | |
|---|---|---|---|---|---|---|
|  | N | GG | GR | RR | G | R |
| ANCA(+) UC | 89 | 89.9 | 9.0 | 1.1 | 94.4 | 5.6 |
| ANCA(−) UC | 25 | 72.0 | 24.0 | 4.0 | 84.0 | 16.0 |
|  |  |  |  |  |  | P = 0.016 |

TABLE 2-continued

Comparisons within UC and within CD as a function of ANCA Status

|  | Genotype (%) | | | Allele (%) | |
| --- | --- | --- | --- | --- | --- |
|  | N | GG | GR | RR | G | R |
| ANCA(+) CD | 27 | 63.0 | 33.3 | 3.7 | 79.6 | 20.4 |
| ANCA(−) CD | 90 | 84.4 | 14.4 | 1.1 | 91.7 | 8.3 |
|  |  |  |  |  |  | P = 0.014 | follow Hardy-Wenberg distributions in all subgroups. When the comparison between ANCA(+) and ANCA(−) groups was made by examining the frequency of patients with or without allele R241, the differences within UC and within CD, as set forth in Table 3, were again significant and odd ratios were 3.5 for ANCA(−) UC and 3.2 for ANCA(+) CD. The Mantel-Haenszel test was performed for stratified analyses.

TABLE 3

Comparisons within UC and within CD stratified on ANCA status(presence or absence of an allele)

R241 allele at codon 241

|  | presence | absence | P | Odd Ratio |
| --- | --- | --- | --- | --- |
|  | N (%) | (%) | value | (95% CI) |
| ANCA(+) UC | 89 10.1 | 89.9 |  | 3.5 |
| ANCA(−) UC | 25 28.0 | 72.0 | 0.023 | (1.2, 10.5) |
| ANCA(+) CD | 27 37.0 | 63.0 |  | 3.2 |
| ANCA(−) CD | 90 15.6 | 84.4 | 0.015 | (1.2, 8.4) |

This G/R 241 polymorphism is of particular significance because it occurs in Ig domain 3 which is demonstrated to be of importance in binding to the Mac-11 form of leukocyte integrin. (See, Diamond, M. S., et al., Cell 65: 961–971, (1991), incorporated herein by reference. As indicated above, the common allele is G241. Glycine is present at the analogous position in ICAM-1 from chimpanzee (Hammond L., McClelland A., unpublished. GenBank Accession No. 86848), dog (Smith, C. W., et al., J. Clin. Invest. 88: 1216–1223 (1991)), mouse (Ballantyne, C. M., et al., Genomics 9: 547–550 (1991)), and rat (Kita, Y., et al., Biochim. Biophys. Acta 1131: 108–111 (1992)), and in human ICAM-3 (Fawcett, J., et al., Nature. 360: 481–84 (1992)) which indicates that the nonconservative substitution of Arg at amino acid residue 241 affects the adhesive function ICAM-1.

In accordance with the present invention, there are provided methods of screening for IBD comprising assaying nucleic acid of a subject for the presence or absence of R241 allele of the ICAM-1 gene, wherein the presence of said R241 allele is indicative of IBD. Both UC and CD may be screened for at the same time, or as in alternative embodiments of the invention, UC and CD may be screened for separately. Nevertheless, the presence of the R241 allele is indicative of these diseases.

The term "nucleic acid" as used herein refers to DNA or RNA. Thus the methods of the present invention may be performed, for example, by using genomic DNA as well as cDNA or mRNA.

Those of skill in the art will understand that there are numerous well known methods to assay for the presence or absence of the G/R 241 polymorphism given the sequence information provided herein. Thus, while exemplary assay methods are described herein, the invention is not so limited.

In one embodiment of the invention, the presence or absence of R241 allele in a subject's nucleic acid can be detected simply by starting with any nucleated cell sample, obtained from a subject, from which genomic DNA, for example, can be isolated in sufficient quantities for analysis. The presence or absence of the R241 allele can be determined by sequence analysis of genomic DNA, accomplished via Maxam-Gilbert or another conventional technique.

In another embodiment of the present invention, assaying for the presence or absence of the R241 allele includes amplification of the subject's nucleic acid, wherein the subject's nucleic acid comprises a sequence that encodes at least nucleotide 778 of ICAM-1 cDNA. Nucleotide 778 of ICAM-1 cDNA encodes (corresponds) to the nucleotide in the first position of codon 241.

The term "encode" in its various grammatical forms as used herein includes nucleotides and/or amino acids which correspond to other nucleotides or amino acids in the transcriptional and/or translational sense, despite the fact that they may not strictly encode for one another. For example, a genomic DNA nucleotide would be considered to "encode" a nucleotide of cDNA (e.g., nucleotide 635 of SEQ ID NO 1 "encodes" or corresponds to nucleotide 778 of SEQ ID NO 2) despite the indirect nature (through mRNA) of that code.

Using the sequence data given in SEQ ID NO 1–5, one can amplify nucleic acid encoding at least nucleotide 778 of ICAM-1 cDNA. The amplified nucleic acid can then be assayed by any of a variety of methods to ascertain the genotype, including for example, allele-specific oligonucleotide probing (ASO), differential restriction endonuclease digestion (DRED), and ligase-mediated gene detection (LMGD).

Additional methods of analysis would also be useful in this context, such as fluorescence resonance energy transfer (FRET) as disclosed by wolf et. al., Proc. Natl. Acad. Sci. USA 85: 8790–94 (1988), the contents of which is incorporated herein by reference.

Amplification of nucleic acid may be achieved using conventional methods, see, e.g., Maniatis, et al., Molecular Cloning: A Laboratory Manual 187–210 (Cold Spring Harbour Laboratory, 1982) which is incorporated herein by reference. For example, mRNA from epithelial cells can be converted to cDNA and then enzymatically amplified to produce microgram quantities of cDNA encoding ICAM-1.

Amplification, however, is preferably accomplished via the polymerase chain reaction ("PCR") method disclosed by U.S. Pat. Nos. 4,698,195 and 4,800,159, the respective contents of which are hereby incorporated herein by reference. More specifically, oligonucleotide primer pairs can be constructed that allow enzymatic amplification of a subject's nucleic acid that encodes at least nucleotide 778 of ICAM-1 cDNA. The amplified nucleic acid can then be assayed to determine the presence or absence of the R241 allele.

Primer pairs suitable for use in the practice of the present invention are linear oligonucleotides ranging in length from about 15 to about 25 nucleotides in length. One of the primers in the pair should be complementary to a nucleotide sequence upstream of the nucleic acid that encodes at least nucleotide 778 of ICAM-1 cDNA. And the other should be complementary to a sequence located down stream of this target site.

The sequences complementary to the primer pairs may be separated by as many nucleotides as the PCR technique will allow. However, one of skill in the art will understand that there are practical limitations of subsequent assaying procedures which may dictate the number of nucleotides between the sequences complementary to the primer pairs. It is presently preferred that the primers are equidistant from the nucleotide(s) targeted for amplification.

A pair of primers suitable for use in the practice of the present invention is set forth in SEQ ID NOS 4 and 5. These primers may be used as a pair or each in combination with another suitable primer. SEQ ID NO 4 is suited for use with genomic DNA and mRNA. The sequence with which the primer of SEQ ID NO 4 anneals is in intron 3 upstream of codon 241. SEQ ID NO 5 is suitable for use with genomic DNA, cDNA or mRNA. The sequence with which the primer of SEQ ID NO 5 anneals is in exon 4 downstream of codon 241.

SEQ ID NO 1 sets forth a representative genomic DNA sequence of exon 3, intron 3, exon 4, intron 4 and exon 5 (in consecutive order reading 5' to 3') for human ICAM-I. SEQ ID NO 2 sets forth a cDNA sequence encoding ICAM-1. From this sequence information, one of skill in the art would be able to produce numerous primers suitable for use in the amplification of nucleic acid sequence encoding at least nucleotide 778 of ICAM-1 cDNA without undue experimentation.

Another embodiment of the invention utilizes allele-specific oligonucleotide ("ASO") probes for the R241 allele and the G241 allele to assay for the presence or absence of R241 allele of the ICAM-1 gene. Accordingly, there is provided a method of screening for IBD, comprising assaying nucleic acid of a subject for the presence or absence of R241 allele of the ICAM-1 gene by contacting the nucleic acid with an R241 allele-specific oligonucleotide probe under conditions suitable to cause the probe to hybridize with nucleic acid encoding the R241 allele of the ICAM-1 gene, but not with nucleic acid encoding the G241 allele of the ICAM-1 gene, and detecting the presence or absence of hybridization.

In yet another embodiment of the present invention, the ASO probe comprises a sequence complementary to a region of SEQ ID NO 1, wherein said region comprises at least the first nucleotide of codon 241 of SEQ ID NO 1. In still another embodiment of the present invention, the ASO probe comprises a sequence complementary to a region of SEQ ID NO 2, wherein said region comprises at least nucleotide 778 of SEQ ID NO.2.

According to conventional ASO procedures, oligonucleotide probes are synthesized that will hybridize, under appropriate annealing conditions, exclusively to a particular amplified nucleic acid sequence that contains a nucleotide(s) that distinguishes one allele from other alleles. The probes are discernably labeled so that when the R241 allele-specific oligonucleotide probe hybridizes to the sequence encoding the R241 allele, it can be detected, and the specific allele is thus identified.

In another embodiment of the invention, either of the subject's amplified nucleic acid or the ASO probes can be bound onto two solid matrixes (e.g., nylon, nitrocellulose membrane and the like) by standard techniques and then each membrane can be placed into separate hybridization reactions with an ASO probe or amplified nucleic acid, respectively. For example, if the amplified nucleic acid were bound onto a solid matrix, one hybridization reaction would utilize an oligonucleotide probe specific for to R241 allele encoding Gly under conditions optimal for hybridization of this probe to its complement. The other hybridization reaction would utilize an oligonucleotide specific to G241 allele encoded by GGG under conditions optimal for hybridization of that probe to its complement. Accordingly, the ASO probes my bear the same label, but will still be distinguishable because they are hybridized in separate chambers.

In this manner, not only can it be determined whether the subject's nucleic acid encodes the R241 allele, but it can also be determine whether the subject is a heterozygote or a homozygote. If an ASO probe is found to bind to subject's nucleic acid on only one membrane, then the subject is homozygous for that particular allele which the ASO probe was designed to bind. If the ASO probes are found to hybridize the subject's nucleic acid on both membranes, then the subject is heterozygous. An example of this technique applied to the detection of cystic fibrosis heterozygotes is Lemna, W. K., et al., N. Eng. J. Med. 322: pp. 291–296 (1990), incorporated herein by reference.

The ASO probes of the present invention can be about 7 to about 35 nucleotides in length, preferably about 15 to 20 nucleotides in length, and are complementary to a nucleic acid sequence encoding at least nucleotide 778 of ICAM-1 cDNA. "R241 ASO probes" are specific for the R241 allele. An example of an "R241 ASO probe" is set forth in SEQ ID NO 7. "G241 ASO probes" are specific for the G241 allele. An example of an "G241 ASO probe" is set forth in SEQ ID NO 6. Those of skill in the art will understand that other ASO probes may be designed using the sequence information provided herein. For probe design, hybridization techniques and stringency conditions, see, Ausubel, et al., (eds.) "Current Protocols in Molecular Biology" Wiley Intersciences, New York, sections 6.3 and 6.4 (1987, 1989), incorporated herein by reference. Additional approaches to probe design and detection can also be used, e.g., ligase-mediated gene detection (LMGD), as disclosed by Landeregren, et al., Science 241: 1077–80 (1988) and fluorescence resonance energy transfer (FRET), as disclosed by Wolf, et al., Proc. Nat. Acad. Sci. (USA) 85: 8790–94 (1988), each of which are incorporated by reference herein.

The ASOs probes may be discernably "labelled." As used herein, the terms "label" in its various grammatical forms refers to single atoms and molecules that are either directly or indirectly involved in the production of a detectable signal to indicate the presence of a complex (e.g. radioisotope, enzyme, chromogenic or fluorogenic substance, a chemiluminescent marker, or the like). Any label can be linked to or incorporated in an ASO probe, These atoms or molecules can be used alone or in conjunction with additional reagents. Such labels are themselves well-known in clinical diagnostic chemistry.

"Conditions suitable to cause the probe to hybridize with nucleic acid encoding the R241 allele of the ICAM-1 gene, but not with nucleic acid encoding the G241 allele of the ICAM-1 gene" is intended to mean that the hybridization reaction conditions should be set for preferential binding of the R241 allele-specific oligonucleotide probe to only the R241 allele and not the G241 allele. One of skill in the art can readily determine such conditions for hybridization based upon the nature of the probe used, factoring into consideration time, temperature, pH and the like.

In still another embodiment of the present invention, there is provided a method of screening for IBD, comprising assaying nucleic acid of a subject for the presence or absence of R241 allele of the ICAM-1 gene comprising cleaving subject's nucleic acid with a restriction endonuclease, wherein said restriction endonuclease differential cleaves nucleic acid encoding R241 allele as compared to nucleic acid encoding G241 allele, and subject's nucleic acid comprises a sequencing encoding at least nucleotide 778 of the ICAM-1 cDNA.

DRED analysis is accomplished in the following manner. If conditions occur including (1) a particular amplified nucleic acid contains a sequence variation that distinguishes an allele of a polymorphism and (2) this sequence variation is recognized by a restriction endonuclease, then the cleavage by the enzyme of a particular nucleic acid sequence can be used to determine the allele. In accomplishing this determination, amplified nucleic acid of a subject is digested and the resulting fragments are analyzed by size or movement through a gel. The presence or absence of nucleotide fragments, corresponding to the endonuclease cleaved fragments, determines which allele is present.

A restriction endonuclease suitable for use in the practice of the present invention can be readily be identified by one of skill in the art, for example, by synthesizing two nucleic acid sequence of equal length which are identical to one other and to 2 cDNA sequence encoding codon 241, except that one sequence encodes the R241 allele and the other encodes the G241 allele. A prospective restriction endonuclease is then contacted with each of the sequences, the sequences are examined and the restriction endonuclease deemed suitable if the two sequences are cleaved differently. The same procedure may be followed to identify restriction endonucleases suitable for use in the practice of the present invention with genomic DNA.

The present invention also provides methods of screening for IBD, comprising assaying nucleic acid of a subject for the presence or absence of R241 allele of the ICAM-1 gene by hybridizing the nucleic acid with a pair of oligonucleotide probes to produce a construct, wherein a first probe of the pair is labeled with a first label and a second probe of the pair is labeled with a second label, such that the first label is distinguishable from said second label, and the probes hybridize adjacent to each other at a nucleotide encoding amino acid residue 241 of ICAM-1. Followed by reacting said construct with a ligase in a reaction medium, and then analyzing said reaction medium to detect the presence or absence of a ligation product comprising said first probe and said second probe.

In the course of an LMGD-type assay, as disclosed by Landegren et al., Science 241: 1077–80 (1988), the contents of which are hereby incorporated by reference, a pair of oligonucleotide probes are synthesized that will hybridize adjacently to each other, for example, on a cDNA segment under appropriate annealing conditions, at the specific nucleotide that distinguishes the R241 allele from the G241 allele of ICAM-1 gene. Each of the pair of specific probes is labeled in a different manner, and when it hybridizes to the allele-distinguishing cDNA segment, both probes can be ligated together by the addition of a ligase.

When the ligated probes are isolated from the cDNA segment, both types of labeling can be observed together, confirming the presence of the R241 allele-specific nucleotide sequence. Where the above-described pair of differently labeled probes bind to a nucleic acid containing a distinguishing nucleotide of the G241 allele, the probe pair is not ligatable and, after the probes are isolated from the cDNA segments, both types of labeling are observed separately.

An exemplary LMGD-type assay for detecting the presence or absence of R241 allele of the ICAM-1 gene in a subject's nucleic acid, in accordance with the present invention, entails the use of a pair of oligonucleotide probes that bind to a nucleic acid adjacent to each other at a nucleotide encoding nucleotide 778 of ICAM-1 cDNA, wherein one probe is radioactively 32P-labeled and the other probe is biotin-labeled. The biotin labeled probe hybridizes nucleotides encoding. 758–778 of ICAM-1 cDNA, wherein nucleotide 778 is an adenine, which distinguishes the R241 allele. The 32P-labeled probe hybridizes nucleotides encoding nucleotides 779–799 of ICAM-1 cDNA and, therefore will hybridize adjacently to the biotin labeled probe. These probes are then added under annealing conditions such that they hybridize adjacently to each other spanning nucleotides encoding nucleotides 758–779 of ICAM-1 cDNA.

When the R241 allele sequence is present in the amplified nucleic acid, then the addition of a ligase will result in the biotin labeled probe being covalently bound to the 32P-labeled probe. The ligation is possible, because the ends of the probes that are adjacent to each other (hybridized to nucleotides 778 and 779) are both hybridized to the nucleotides encoding the ICAM-1 cDNA. In the case where these two probes hybridize to the G241 allele, the biotin-labeled probe end at nucleotide 778 is not hybridized appropriately, preventing the ligation step from occurring.

When this pair of probes binds completely to the nucleic acid encoding R241 allele, therefore, the probes are ligated and when the probes are separated from the nucleic acid encoding R241 allele and exposed so as to be detected, both the biotin/strepavidin and the 32P-labeling are present together. When the G241 allele sequence is hybridized, on the other hand, the probes cannot be ligated, and the biotin/strepavidin-and 32P-labeling are observed separately. In this manner, R241 allele and G241 allele can be distinguished.

The invention further includes antibodies which are capable of binding ICAM-1 encoded by R241 allele, but not to ICAM-1 encoded by G241 allele. Such an antibody may be easily produced by one of skill in the art by preparing a peptide, protein conjugate which is specific to the unique amino acid in ICAM-1 encoded by R241 allele and immunizing an animal as discussed below. The invention includes the hybridoma cell line which produces the antibody of the same specificity, the antibody produced by the hybridoma cell line and the method of production.

Antibodies raised against the R241 allele or ICAM-1 encoded by the R241 allele are expected to have utility in the diagnosis, prevention and treatment of IBD. In this context, the term "antibody" encompasses monoclonal antibodies, polyclonal antibodies and humanized antibodies. Preferably, for therapeutic applications, the antibodies employed will be humanized, monoclonal antibodies.

The above-described antibodies can be prepared employing standard techniques, as are well known to those of skill in the art, using R241 allele or ICAM-1 encoded by the R241 allele ("R241 ICAM-1"), or fragments thereof, as antigens for antibody production. Antibodies of the present invention are typically produced by immunizing a mammal with an inoculum containing R241 ICAM-1, or fragments there of and thereby inducing in the mammal antibody molecules having immunospecificity for R241 ICAM-1 or polypeptide fragment thereof.

For example, antibodies raised in rabbits against a synthetic peptide recognize the synthetic peptide and the R241 ICAM-1 on an equimolar basis, and, preferably, they are capable of inhibiting the activity of the native protein. Antibodies to R241 ICAM-1 may be obtained, for example, by immunizing three month old male and female white New Zealand rabbits with the synthetic peptide or fragment thereof to which Tyr has been added at the C-terminus in order to couple it, as an antigen, to BSA by a bisdiazotized benzidine (BDB) linkage by reaction for 2 hours at 4° C. The reaction mixture is dialyzed to remove low molecular weight material, and the retenate is frozen in liquid nitrogen and stored at −20° C. Animals are immunized with the equivalent of 1 mg of the peptide antigen according to the procedure of Benoit et al. P.N.A.S. USA, 79, 917–921 (1982), incorporated herein by reference. At four week intervals, the animals are boosted by injections of 200 µg of the antigen and bled ten to fourteen days later. After the third boost, antiserum is examined for its capacity to bind radioiodinated antigen peptide prepared by the chloramine-T method and then purified by CMC-ion exchange column chromatography. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

A radioimmunoassay is established with the antisera and serum from subsequent bleeds from the same rabbits. The native protein is recognized by the antibodies on an equimolar basis as compared to the synthetic peptide antigen.

In the case of monoclonal antibody production, one proceeds by isolating lymphocytes and fusing them with myeloma cells, producing hybridomas. The cloned hybridomas are then screened for production of antibodies specific for sequences encoded by the R241 allele.

The antibody so produced can be used, *inter alia*, in diagnostic methods and assay methods to detect the presence or absence of nucleic acid encoding the R241 allele. Thus methods of screening IBD are contemplated comprising assaying a tissue sample from a subject for the presence or absence of arginine at amino acid residue 241 of ICAM-1 wherein the presence of arginine at amino acid residue 241 of ICAM-1 is indicative of IBD. A "tissue sample" suitable for use in the practice of the present invention includes any cell samples, bodily fluids or fractions thereof which contain ICAM-1 and, for example, preferably including epithelial cells.

One such method employs an "ELISA" format to detect the presence or absence of arginine at amino acid residue 241 of ICAM-1. "ELISA" refers to an enzyme-linked immunosorbent assay that employs an antibody or antigen immobilized on solid matrix and an enzyme-antigen or enzyme-antibody conjugate to detect and quantify the amount of an antigen present in a sample. A description of the ELISA technique is found in Chapter 22 of the 4th Edition of *Basic and Clinical Immunolocy* by D. P. Sites et al., published by Lange Medical Publications of Los Altos, Calif. in 1982 and in U.S. Pat. No. 3,654,090, U.S. Pat. No. 3,850,752; and U.S. Pat. No. 4,016,043, which are all incorporated herein by reference.

Thus, in preferred a embodiment a tissue sample from the test subject is contacted with immobilized lymphocyte function-associated antigen-1 ("LFA-1"), for example, and an enzyme-labelled antibody specific for R241 ICAM-1 under conditions suitable to form a complex of LFA-1, ICAM-1 and said labelled antibody. Unbound labelled antibody is separated from said complex, and the presence or absence of arginine at amino acid residue 241 of ICAM-1 is detected by measuring the presence or absence of bound, labelled antibody. This method may be modified by use of a non-enzyme label.

Alternatively, a ligand, other than LFA-1, which is recognized by ICAM-1, or a non-R241 specific antibody or the like, may be immobilized on a solid matrix, for example. Such reagent are typically immobilized on a solid matrix by adsorption from an aqueous medium although other modes of affixation applicable to proteins and polypeptides well known to those skilled in the art can be used.

Useful solid matrices are also well known in the art. Such materials are water insoluble and include cross-linked dextran (available from Pharmacia Fine Chemicals; Piscataway, N.J.); agarose; beads of polystyrene about 1 micron to about 5 millimeters in diameter (available from Abbott Laboratories; North Chicago, Ill.); polyvinyl chloride; polystyrene; cross-linked polyacrylamide; nitrocellulose- or nylon-based webs such as sheets, strips or paddles; or tubes, plates or the wells of a microtiter plate such as those made from polystyrene or polyvinylchloride.

The anti-R241 ICAM-1 antibodies can also be used for the immunoaffinity or affinity chromatography purification of ICAM-1 biological materials. In addition, an anti-R241 ICAM-1 antibody according to the present invention can be used in mammalian therapeutic methods, preferably human, as a R241 ICAM-1 agonist or to neutralize or modulate the effect of R241 ICAM-1.

"Antibody" also encompasses fragments, like Fab and F(ab')2, of anti-R241 ICAM-1 antibodies, and conjugates of such fragments, and so-called "antigen binding proteins" (single-chain antibodies) which are based on anti-R241 ICAM-1 antibodies, in accordance, for example, with U.S. Pat, No. 4,704,692, incorporated herein by reference.

Antibodies against ICAM-1 encoded by the R241 allele can also be employed in the generation, via conventional methodology, of anti-idiotypic antibodies (antibodies that bind an anti-ICAM-1 allele antibody), e.g., by the use of hybridomas as described above. See, for example, U.S. Pat. No. 4,699,880. Such anti-idiotypic antibodies could be used to sequester anti-R241 ICAM-1 antibodies in an individual, thereby treating or preventing pathological conditions which 20 may be associated with an immune response whereby R241 allele is recognized as "foreign" by the immune system of the individual.

The present invention further includes methods of inhibiting leukocyte function-associated antigen-1 ("LFA-1") and R241 ICAM-1 interaction, comprising the step of contacting R241 ICAM-1 containing cells with antibody specific for R241 ICAM-1.

The present also provides methods for treating IBD comprising administering a therapeutically effective dose of an antibody which recognizes and binds R241 ICAM-1 wherein the R241 ICAM-1 function is modified. Antibodies suitable for use in these therapeutic methods need not be raised specifically against R241 allele and may include, for example, the murine anti-ICAM-I mAb (BIRR1) currently being tested by A. Kavanaugh, L. Nichols, L. Davis, R. Rothiem and P. Lipsky of the Univ. of Texas, Southwestern Medical Center, Dallas, Tex. Alternatively or in conjunction with treatment methods described above, IBD may be treated in accordance with the presence invention by administering a therapeutically effective dose of antisense oligonucleotide complementary to nucleic acid encoding R241 allele of the ICAM-1 gene.

Antisense oligonucleotides can be prepared as polynucleotides complementary to (a) nucleotide sequences comprising a DNA which encodes R241 allele or (b) nucleotide sequences comprising R241 allele messenger RNA (mRNA). For both types, the length an antisense oligonucleotide of the present invention is not critical so long as there is no promoter sequence (for DNA) or Shine-Delgarno site (for RNA) present. Type (a) antisense oligonucleotides would be synthesized de novo, for example, based on knowledge concerning the nucleotide sequence of the genomic DNA shown in SEQ ID NO 1. Type (b) antisense oligonucleotides could also be produced de novo (DNA or RNA), or by transforming an appropriate host organism with DNA that is transcribed constitutively into RNA which binds an ICAM-1 allele mRNA. Both type (a) and type (b) oligonucleotides within the present invention are expected to be useful as agents for "down-regulating" (turning off) the expression of ICAM-1 on the cell surface, or inhibiting either transcription [type (a)] or translation [type (b)].

The present invention contemplates therapeutic compositions useful for practicing the therapeutic methods described herein. Therapeutic compositions of the present invention may contain a physiologically tolerable carrier together with a ICAM-I antisense oligonucleotide or anti-ICAM-1 antibody, as described herein, dissolved or dispersed therein as an active ingredient. In a preferred embodiment, the therapeutic composition is not immunogenic when administered to a mammal or human patient for therapeutic purposes. To some extent this may be accomplished, for example, by commonly known techniques of "humanizing" antibodies wherein the constant regions of a antibody derived from an animal is replaced with constant regions from a human.

As used herein, the term "pharmaceutically acceptable" and grammatical variations thereof, as they refer to compositions, carriers, diluents and reagents, are used to represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, is hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutically effective amount is a predetermined amount calculated to achieve the desired effect, i.e., down regulation of the inflammatory response in the gut which is mediated by ICAM-1. The required dosage will vary with the particular treatment and with the duration of desired treatment.

Those of skill in the art will appreciate that any of the foregoing inventive methods may be used not only to screen for IBD, but also to predict a subject's susceptability to IBD. There is general agreement that genetics are important in a person's susceptibility to UC and CD. Evidence supporting this conclusion include consistent ethnic differences which cross different geographic areas, dramatic familial aggregation, existence of genetic syndromes that feature IBD, higher monozygotic than dizygotic twin concordance rates, lack of increased frequency in spouses, affected relatives separated in space and time, and associations between IBD and genetic markers. Thus any of the inventive methods for screening for IBD may also be used as an initial screening tool to predict a subject's susceptibility to IBD.

These methods for determining susceptibility to IBD are particularly useful in combination with a subject's family history of IBD. For example, a parent suffering from IBD and who has a family history of IBD, may well have a child who is susceptible to IBD, but who has not yet shown symptoms. To alleviate the concern of the parent, as well as the child, and to take any preventative measures which might delay or prevent onset, one of the many inventive methods provided herein can be used to determine whether the child is a carrier of the R241 allele. If so, further testing can be performed, for example, ANCA status can be determined to provide further support for the predicted susceptibility.

Similarly, the screening methods provided herein are preferably used in combination with existing methods for diagnosing IBD (e.g. endoscopic, histologic, radiologic, and in particular determination of ANCA status) to maximize a confidence in the ultimate diagnosis regarding IBD.

Kits for use in (1) screening for IBD, (2) screening for susceptibility to IBD, and (3) treating IBD are also provided by the present invention. Such kits can include all or some of the reagents primers, probes, antibodies and antisense oligonucleotides described herein for determining the presence or absence of nucleic acid encoding R241 allele or for treatment of IBD. Kits of the present invention may contain, for example, restriction endonuclease, one or more labeled oligonucleotide probes that distinguish nucleic acid encoding nucleotide 778 of ICAM-1 cDNA, ligase, R241 allele-specific oligonucleotide probe, primer for amplification of nucleic acid encoding at least nucleotide 778 of ICAM-1 cDNA, means for amplifying a subject's nucleic acid encoding at least nucleotide 778 of ICAM-1 cDNA, neutrophil, alkaline phosphatase coupled goat anti-human gamma chain specific antibody, fluorescein-labelled goat anti-human gamma chain specific antibody, anti-human gamma chain specific antibody, antisense oligonucleotides, antibody specific for, or which binds R241 ICAM-I, or combinations of any of the above.

As amenable, these suggested kit components may be packaged in a manner customary for use by those of skill in the art. For example, these suggested kit components may be immobilized on a solid matrix or provided in solution or as a liquid dispersion or the like.

A presently preferred embodiment of the inventive kits for use in screening for IBD or determining susceptibility to IBD comprises R241 allele-specific oligonucleotide probe immobilized on a solid matrix, neutrophil immobilized on solid matrix and alkaline phosphatase-coupled goat anti-human gamma-chain specific antibody.

The invention will now be described in greater detail by reference to the following non-limiting examples.

A. EXAMPLES

1. Determination of the G/R 241 Point Mutation for ICAM-1

The identification of the G/R 241 allele of ICAM-1 was performed by amplification of genomic DNA followed by direct sequencing of the PCR product using an ABI automated sequencer. Additional sequencing information was obtained from published literature (Stauton, et al., *Cell* 52: 925–933 (1988); Tomassini, et al., *Proc. Natl. Acad. Sci. U.S.A.* 86: 4907–4911 (1989) and GenBank (Burks, et al., *Nucleic Acids Res. (Suppl.)* 20: 2065–2069 (1992).

Amplification of the genomic DNA was performed in 20 μl reactions under the following conditions: 10 mM Tris HCl at pH 8.3, 50 mM KCl, 1.5 mM $MgCl_2$, 200 μM each dNTP, 10 μM each primer, 50 ng genomic DNA, and 0.5 units of Amplitaq polymerase (Perkin-Elmer Cetus, Norwalk, Conn.). PCR conditions were as follows: denaturing polynucleotide strands at 94° C. for 1 min, annealing primers at 52° C. for 45 sec, and primer extending at 72° C. for 45 sec for 26 cycles. One primer for each reaction was end labeled with [$-^{32}P$] ATP using T4 polynucleotide kinase. The reaction products were analyzed on a 6% denaturing polyacrylamide gel as describe in Weber, J. L. and May, P. E., *Am. J. Hum. Genet.* 44: 388–396 (1989) and incorporated by reference herein. The size of alleles as generated by PCR were determined using a dideoxy sequencing ladder produced from M13 DNA as a template.

2. Amino Acid Polymorphisms Analysis of ICAM-1 a. Amplification of ICAM-1 Encoding DNA for Screening Methods

In order to examine genomic DNA for R241 allele of the ICAM-1 gene, the polymerase chain reaction was used to amplify a region of the ICAM-1 gene encoding amino acid 241 which is near the junction of intron 3 and exon 4. A pair of primers were constructed: 5'-GATTGAAGAAGCCAGCAG-3' (SEQ ID NO 4) complements genomic DNA encoding intron 3 of the ICAM-1 gene, and 5'-GTCGTTGCCATAGGTGAC-3' (SEQ ID NO 5) complements genomic DNA encoding exon 4 of the ICAM-1 gene, SEQ ID NO 1.

Amplification of the genomic DNA was performed in 20 μl reactions under the following conditions: 10 mM Tris HCl at pH 8.3, 50 mM KCl, 1.5 mM $MgCl_2$, 200 μM each dNTP, 10 μM each primer, 50 ng genomic DNA, and 0.5 units of Amplitaq polymerase (Perkin-Elmer Cetus, Norwalk, Conn.). The conditions for PCR amplification were as follows: denaturing polynucleotide strands at 94° C. for 30 sec, annealing primers at 55° C. for 30 sec, and primer extending at 72° C. for 45 sec for 40 cycles.

b. Screening with Allele Specific Oligonucleotides

Three μl of the PCR product was applied to a Hybond N+ membrane using a Beckman Biomek robot (CITY AND STATE). The membranes were air dried and treated with denaturing solution (0.5 N NaOH) for 15 min followed by renaturation in 2×SSC with 0.4 M Tris at pH7.5 for 10 min. Allele specific oligonucleotides were 5'-TCCCTGGACGGGCTGTTCC-3' (SEQ ID NO 6) to detect the G241 allele and 5'-TCCCTGGACAGGCTGTTCC-3' (SEQ ID NO 7) to detect the R241 allele. Oligonucleotides were end labeled with [$\gamma-^{32}P$] ATP, and the membranes were prehybridized with buffer (10% polyethylene glycol, 7% SDS, 1% bovine serum albumin, 250 mM NaCl and 250 mM sodium phosphate) at 65° C. and hybridized with $2-3\times10^6$ cpm/10 ml of the labeled ASO and 20 fold higher concentration of the nonradioactive ASO for the alternate allele. Hybridization was at 65° C. for 30 min and hybridization was continued subsequently at 37° C. The membranes were washed with 5×SSC at room temperature followed by 2×SSC at 45° C. for 30 min and used for autoradiography.

3. Detection of ANCAS by ELISA

The development and validation of the fixed neutrophil ELISA has been described in detail by Saxon, et al., *J. Allergy Clin. Immunol.* 86: 202–10 (1990) which is incorporated herein by reference.

Purified neutrophils from a single normal individual served as the source of antigen for the fixed-neutrophil ELISA assay. Neutrophils were isolated as follows.

a. Separation of Human Peripheral Blood Lymphocytes by Ficoll-Hypacue Gradient Centrifugation A Ficoll-Hypaque solution having a specific gravity of 1.080 was made by vigorously combining 31.8 g Ficoll 400 (Pharmacia, Sweden) and 400 ml deionized $H_2O$ and then mixing in 100 ml of 50% sodium diatrizoate hypaque (UCLA Pharmacy, Los Angeles, Calif.). The Ficoll-hypaque solution was then filter-sterilize through a 0.22 or 0.45 um bottle top filter. (The Ficoll-hypaque solution may be stored at 4° C., protected from light.)

15 ml of the Ficoll-hypaque solution were poured into a 50 ml conical centrifuge tube and 30 ml heparinized blood was carefully laid over it. The contents was centrifuge at 1000×g (2000 RPM) for 20 min. The resulting interface was removed using a serologic pipet or pasteur pipet and placed into a second 50 ml conical centrifuge tube. The interface layer was then diluted with at least an equal volume of Hanks' Balanced Salt Solution (HBSS) (Irvine Scientific, Santa Ana, Calif.) and centrifuged at 400×g (1200 RPM) for 5 min. Removal of the interface, dilution and centrifugation was repeated twice again. Finally, the cell pellet was resuspended in RPMI 1640 (Irvine Scientific, Santa Ana, Calif.) +5% fetal calf serum (GIBCO, Gathersberg, Md.).

b. Isolation of Neutrophil

Using a pipet, serum and remaining Ficoll-Hypaque were carefully removed from red blood cell pellet resulting from procedure described immediately above. 10 ml 6% dextran was added to 15 milliliters of pellet. 1×HBSS was added to reach a final volume of 50 ml. The pellet was re-suspended and the red blood cells were allowed to settle, approximately 45 minutes to one hour.

The supernatant was then retrieved and the pellet discarded. The supernatant was topped off with 1×HBSS to 50 ml and centrifuge for 5 minutes at 1800 rpm. The supernatant was decanted and pellet tapped. The remaining red blood cells were hypotonically lysed by adding 9 ml deionized water, swirling, adding 1 ml 10×HBSS and immediately diluting with 1×HBSS to 50 ml. This was centrifuged for 5 minutes at 1000 rpm. The supernatant was discarded and the pellet re-suspend in 15 ml 1×HBSS.

c. Immobilization of Neutrophil on Microtiter Plate

Microtiter wells (Immulon 2™, Dynatech Labs, Alexandria, Va.) were coated with a monolayer of neutrophils by the addition of 100 μl/well of HBSS containing 250,000 neutrophils (isolated as described above). After the cells had settled and spread for 30 min at room temperature, the microtiter plates were centrifuged at 1000 rpm (300 g) for 5 min, the supernatant was aspirated from the wells, and the plates were air dried. The cells were fixed with 100% methanol for 10 min, after which the plates were air dried and stored at −20° C.

d. Fixed Neutrophil ELISA

For use, the plates were brought to room temperature, and 150 μl of 0.25% bovine serum albumin in phosphate buffered saline (BSA/PBS) was added to each microtiter well for 1 hr to block non-specific binding. The blocking materials was discarded, and 100 μl of test serum diluted in BSA/PBS (or BSA/PBS alone for blank wells) was added. To standardize the assay, a positive pool of sera from 6 individuals with UC (3 with very high and 3 with intermediate levels of ANCA) was used. This was included on each microtiter plate at a dilution of 1:100. The plates were incubated for 1 hr at room temperature in a humidified box (sufficient humidity to minimize volume loss).

The wells were then washed 3 times with 0.05% Tween 20 in PBS (PSB/Tween), and 100 μl/well of a 1:750 dilution of alkaline phosphatase coupled goat anti-human gamma chain specific antibody (Tago, Burlingame, Calif.) in BSA/PBS was added. The wells were allowed to incubate for 1 hr at room temperature in a humidified box. This antibody was discarded, and the wells were washed 3 times with PBS/Tween and 4 times with 0.05M Tris base in 0.9M NaCl, pH 7.5.

Substrate solution (1.5 mg/ml disodium p-nitrophenol phosphate in 0.01M Tris base, 0.0025M MglC2, pH 8.6, 100 μl/well) was added, and color development was allowed to proceed until absorbance at 405 nm in the positive control wells was 0.8–1.0 optical density units greater than in blank wells. Plates were read plate at 405 nm in an EMAX Microplate Reader (Molecular Devices, Menlo Park, Calif.).

3. Confirmation of Positive ELISA Values by Indirect Immunofluorescence

Sera that exhibited levels of binding greater than 2 Standard deviations above the mean level for the normal laboratory controls at a dilution of 1/100 in the ELISA were regarded as being positive and were also examined by indirect immunofluorescence to confirm that the antibody binding was cell-specific.

Approximately 100,000 neutrophils/slide were applied to slides using a cytocentrifuge (Cytospin 3™, Shandon, Inc. Pittsburgh, Pa.) at 500 rpm for 5 minutes. Neutrophils were fixed in 100% methanol at room temperature. The methanol was discarded and coded sera were tested at a dilution of 1:20 in BSA/PBS and stained with fluorescein-labelled F(ab')2 anti human gamma chain specific antibody. The antibody was rinsed off with 100–250 ml phosphate buffered saline. The slides were soaked for 5 minutes in 100–250 ml phosphate buffered saline and then allowed to air dry. The fluorescence pattern was read on a fluorescence microscope at 40×.

Although the invention has been described with reference to presently preferred embodiments, it should be understood that various modifications can be made without departing from the spirit of the invention.

Summary of Sequences

Sequence ID No. 1 is a representative genomic DNA sequence of exon 3, intron 3, exon 4, intron 4 and exon 5 (in consecutive order reading 5' to 3') for human ICAM-I encoding the G241 allele at nt 635 to 637.

Sequence ID No. 2 is a cDNA sequence encoding the R241 allele of the ICAM-1 gene.

Sequence ID No. 3 is an amino acid sequence for ICAM-1 encoded by an R241 allele of the ICAM-1 gene which was derived from the cDNA sequence set forth in SEQ ID NO. 2.

Sequence ID No. 4 is a nucleic acid sequence of a primer suitable for amplification of genomic nucleic acid encoding the R241 allele of the ICAM-1 gene.

Sequence ID No. 5 is the nucleic acid sequence of a primer suitable for use in amplification of nucleic acid encoding the R241 allele of the ICAM-1 gene.

Sequence ID No. 6 is a nucleic acid sequence of an allele-specific oligonucleotide probe suitable for use in detecting the presence or absence of nucleic acid encoding a G241 allele of the ICAM-1 gene. Sequence ID NO 7 is a nucleic acid sequence . . . encoding an R241 allele.

---

We claim:

1. A kit for use in screening for inflammatory bowel disease, comprising an antibody or fragment thereof, said antibody or fragment thereof specifically reactive with ICAM-1 encoded by an R241 ICAM-1 allele but not specifically reactive with ICAM-1 encoded by a G241 ICAM-1 allele, and further comprising means for amplifying nucleic acid encoding all or part of an ICAM-1, wherein said nucleic acid comprises at least nucleotide 721 of ICAM.

2. The kit in accordance with claim 1, wherein said amplifying means comprises:
   (a) a primer oligonucleotide selected from a group consisting of: SEQ ID NO: 4 and SEQ ID NO: 5; and
   (b) reagents necessary to perform PCR.

3. A composition, comprising an antibody or fragment thereof, said antibody or fragment thereof specifically reactive with ICAM-1 encoded by an R241 ICAM-1 allele but not specifically reactive with ICAM-1 encoded by a G241 ICAM-1 allele.

4. The composition of claim 3, which is monoclonal.

5. The composition of claim 3, which is polyclonal.

6. The composition of claim 3, which is a humanized antibody or fragment thereof.

7. The composition of claim 3, which is a fragment selected from the group consisting of Fab and F(ab')2.

8. The composition of claim 3, which is a single chain antibody.

9. The composition of claim 3, further comprising a label.

10. A kit for use in screening for inflammatory bowel disease, comprising an antibody or fragment thereof, said antibody or fragment thereof specifically reactive with ICAM-1 encoded by an R241 ICAM-1 allele but not specifically reactive with ICAM-1 encoded by a G241 ICAM-1 allele.

11. A method of diagnosing inflammatory bowel disease (IBD) in a subject, comprising:

(a) contacting a sample from said subject with an antibody or fragment thereof, said antibody or fragment thereof specifically reactive with ICAM-1 encoded by an R241 ICAM-1 allele but not specifically reactive with ICAM-1 encoded by a G241 ICAM-1 allele; and (b) assaying for the presence or absence of arginine at amino acid 241 of ICAM-1 in said sample by detecting specific binding of said antibody or fragment thereof, wherein the presence of arginine at amino acid 241 of ICAM-1 indicates that said subject has IBD.

12. The method of claim 11, wherein step (b) comprises an enzyme-linked immunosorbent assay (ELISA).

13. The method of claim 11, wherein step (a) further comprises contacting said sample with an ICAM-1 ligand to form a tertiary complex.

14. The method of claim 13, wherein said ICAM-1 ligand is lymphocyte function-associated antigen-1 (LFA-1).

15. The method of claim 13, wherein said ICAM-1 ligand is immobilized on a solid matrix.

16. The method of claim 14, wherein said LFA-1 is immobilized on a solid matrix.

17. The method of claim 11, wherein said antibody or fragment thereof is monoclonal.

18. The method of claim 11, wherein said antibody or fragment thereof is polyclonal.

19. The method of claim 11, wherein said antibody or fragment thereof is humanized.

20. The method of claim 11, wherein said antibody or fragment thereof is a fragment selected from the group consisting of Fab and F(ab')2.

21. The method of claim 11, wherein said antibody or fragment thereof is labeled.

22. The method of claim 21, wherein said antibody or fragment thereof is labeled with an enzyme label.

23. The method of claim 21, wherein said antibody or fragment thereof is labeled with a non-enzyme label.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1176 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
CCTGAGGTCT TGCCCACCTT GACCGTGGGG AGGGGAGAAC CGTCGGTCAC CCGTTCTTGG      60
AATGGGATGC GACGGTCCAC CTCCCACCCC GTGGGGCCCG GTTGGAGTGG CACCACGACG     120
AGGCACCCCT CTTCCTCGAC TTTGCCCTCG GTCGACACCC CCTCGGGCGA CTCCAGTGCT     180
GGTGCCACGA CCACTCCTCT CTAGTGGTAC CTCGGTTAAA GAGCACGGCG TGACTTGACC     240
TGGACGCCGG GGTTCCCGAC CTCGACAAAC TCTTGTGGAG CCGGGGATG GTCGAGGTCT      300
GGAACACTCC TAACTTCTTC GGTCGTCCCT CTTCCACCCC CACCCCATAG GACGTTACGC     360
CACTGGACAC CGGTGTCCTA GAAAACTCTA CCCACACCGG GGCCGATTCC CCACGTACAC     420
AAGATCCGCA TACACTGGAT CCGACGACTC ACCGGGACCT TCTCCTAGAG CGTCCTCCCC     480
CTTACTTTAC GGGGTCTCTT CCCGAAGCCC TGCAGGTAGG GACAGACGAG TGTGGAAAGA     540
AGAGAGGGAT CAGGACGGTC GCTGAGGGGG TGTTGAACAG TCGGGGGCCC AGGATCTCCA     600
CCTGTGCGTC CCCTGGCACC AGACAAGGGA CCTGCCCGAC AAGGGTCAGA GCCTCCGGGT     660
CCAGGTGGAC CGTGACCCCC TGGTCTCCAA CTTGGGGTGT CAGTGGATAC CGTTGCTGAG     720
GAAGAGCCGG TTCCGGAGTC AGTCACACTG GCGTCTCCTG CTCCCGTGGG TCGCCGACTG     780
CACACGTCAT TATGACCCCT TGGTCTCGGT CCTCTGTGAC GTCTGTCACT GGTAGATGTC     840
ATTCTTCCCC GTCCCGCCT CACCCCGAAG AACCCCACA CTGGACTTGG GCCCCGCCCC       900
GAGTGACACA CGGATAAGGT CCGAAAGGCC GCGGGTTGCA CTAAGACTGC TTCGGTCTCC     960
AGAGTCTTCC CTGGCTCCAC TGTCACTTCA CACTCCGGGT GGGATCTCGG TTCCACTGCG    1020
ACTTACCCCA AGGTCGGGTC GGTGACCCGG GCTCCCGGGT CGAGGACGAC TTCCGGTGGG    1080
GTCTCCTGTT GCCCGCGTCG AAGAGGACGA GACGTTGGGA CCTCCACCGG CCGGTCGAAT    1140
ATGTGTTCTT GGTCTGGGCC CTCGAAGCAC AGGACA                              1176
```

(2) INFORMATION FOR SEQ ID NO:2:

(i) SEQUENCE CHARACTERISTICS:
        (A) LENGTH: 1599 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1596

(xi) SEQUENCE DESCRIPTION: SEQ ID NO:2:

```
ATG GCT CCC AGC AGC CCC CGG CCC GCG CTG CCC GCA CTC CTG GTC CTG       48
Met Ala Pro Ser Ser Pro Arg Pro Ala Leu Pro Ala Leu Leu Val Leu
  1               5                  10                  15

CTC GGG GCT CTG TTC CCA GGA CCT GGC AAT GCC CAG ACA TCT GTG TCC       96
Leu Gly Ala Leu Phe Pro Gly Pro Gly Asn Ala Gln Thr Ser Val Ser
             20                  25                  30

CCC TCA AAA GTC ATC CGT CCC CGG GGA GGC TCC GTG CTG GTG ACA TGC      144
Pro Ser Lys Val Ile Arg Pro Arg Gly Gly Ser Val Leu Val Thr Cys
         35                  40                  45

AGC ACC TCC TGT GAC CAG CCC AAG TTG TTG GGC ATA GAG ACC CCG TTG      192
Ser Thr Ser Cys Asp Gln Pro Lys Leu Leu Gly Ile Glu Thr Pro Leu
     50                  55                  60
```

```
CCT AAA AAG GAG TTG CTC CTG CCT GGG AAC AAC CCG AAG GTG TAT GAA        240
Pro Lys Lys Glu Leu Leu Leu Pro Gly Asn Asn Pro Lys Val Tyr Glu
 65                  70                  75                  80

CTG AGC AAT GTG CAA GAA GAT AGC CAA CCA ATG TGC TAT TCA AAC TGC        288
Leu Ser Asn Val Gln Glu Asp Ser Gln Pro Met Cys Tyr Ser Asn Cys
                     85                  90                  95

CCT GAT GGG CAG TCA ACA GCT AAA ACC TTC CTC ACC GTG TAC TGG ACT        336
Pro Asp Gly Gln Ser Thr Ala Lys Thr Phe Leu Thr Val Tyr Trp Thr
                    100                 105                 110

CCA GAA CGG GTG GAA CTG GCA CCC CTC CCC TCT TGG CAG CCA GTG GGC        384
Pro Glu Arg Val Glu Leu Ala Pro Leu Pro Ser Trp Gln Pro Val Gly
                115                 120                 125

AAG AAC CTT ACC CTA CGC TGC CAG GTG GAG GGT GGG GCA CCC CGG GCC        432
Lys Asn Leu Thr Leu Arg Cys Gln Val Glu Gly Gly Ala Pro Arg Ala
130                 135                 140

AAC CTC ACC GTG GTG CTC CTC CGT GGG GAG AAG GAG CTG AAA CGG GAG        480
Asn Leu Thr Val Val Leu Leu Arg Gly Glu Lys Glu Leu Lys Arg Glu
145                 150                 155                 160

CCA GCT GTG GGG GAG CCC GCT GAG GTC ACG ACC ACG GTG CTG GTG AGG        528
Pro Ala Val Gly Glu Pro Ala Glu Val Thr Thr Thr Val Leu Val Arg
                165                 170                 175

AGA GAT CAC CAT GGA GCC AAT TTC TCG TGC CGC ACT GAA CTG GAC CTG        576
Arg Asp His His Gly Ala Asn Phe Ser Cys Arg Thr Glu Leu Asp Leu
                180                 185                 190

CGG CCC CAA GGG CTG GAG CTG TTT GAG AAC ACC TCG GCC CCC TAC CAG        624
Arg Pro Gln Gly Leu Glu Leu Phe Glu Asn Thr Ser Ala Pro Tyr Gln
                195                 200                 205

CTC CAG ACC TTT GTC CTG CCA GCG ACT CCC CCA CAA CTT GTC AGC CCC        672
Leu Gln Thr Phe Val Leu Pro Ala Thr Pro Pro Gln Leu Val Ser Pro
210                 215                 220

CGG GTC CTA GAG GTG GAC ACG CAG CGG ACC GTG GTC TGT TCC CTG GAC        720
Arg Val Leu Glu Val Asp Thr Gln Arg Thr Val Val Cys Ser Leu Asp
225                 230                 235                 240

GGG CTG TTC CCA GTC TCG GAG GCC CAG GTC CAC CTG GCA CTG GGG GAC        768
Gly Leu Phe Pro Val Ser Glu Ala Gln Val His Leu Ala Leu Gly Asp
                245                 250                 255

CAG AGG TTG AAC CCC ACA GTC ACC TAT GGC AAC GAC TCC TTC TCG GCC        816
Gln Arg Leu Asn Pro Thr Val Thr Tyr Gly Asn Asp Ser Phe Ser Ala
                260                 265                 270

AAG GCC TCA GTC AGT GTG ACC GCA GAG GAC GAG GGC ACC CAG CGG CTG        864
Lys Ala Ser Val Ser Val Thr Ala Glu Asp Glu Gly Thr Gln Arg Leu
                275                 280                 285

ACG TGT GCA GTA ATA CTG GGG AAC CAG AGC CAG GAG ACA CTG CAG ACA        912
Thr Cys Ala Val Ile Leu Gly Asn Gln Ser Gln Glu Thr Leu Gln Thr
290                 295                 300

GTG ACC ATC TAC AGC TTT CCG GCG CCC AAC GTG ATT CTG ACG AAG CCA        960
Val Thr Ile Tyr Ser Phe Pro Ala Pro Asn Val Ile Leu Thr Lys Pro
305                 310                 315                 320

GAG GTC TCA GAA CGG ACC GAG GTG ACA GTG AAG TGT GAG GCC CAC CCT       1008
Glu Val Ser Glu Arg Thr Glu Val Thr Val Lys Cys Glu Ala His Pro
                325                 330                 335

AGA GCC AAG GTG ACG CTG AAT GGG GTT CCA GCC CAG CCA CTG GGC CCG       1056
Arg Ala Lys Val Thr Leu Asn Gly Val Pro Ala Gln Pro Leu Gly Pro
                340                 345                 350

AGG GCC CAG CTC CTG CTG AAG GCC ACC CCA GAG GAC AAC GGG CGC AGC       1104
Arg Ala Gln Leu Leu Leu Lys Ala Thr Pro Glu Asp Asn Gly Arg Ser
                355                 360                 365

TTC TCC TGC TCT GCA ACC CTG GAG GTG GCC GGC CAG CTT ATA CAC AAG       1152
Phe Ser Cys Ser Ala Thr Leu Glu Val Ala Gly Gln Leu Ile His Lys
```

|     |     |     |     |     |     |     |     |     |     |     |     |     |     |
| --- | --- | --- | --- | --- | --- | --- | --- | --- | --- | --- | --- | --- | --- |
|     | 370 |     |     |     | 375 |     |     |     | 380 |     |     |     |     |
| AAC | CAG | ACC | CGG | GAG | CTT | CGT | GTC | CTG | TAT | GGC | CCC | CGA | CTG GAC GAG | 1200 |
| Asn | Gln | Thr | Arg | Glu | Leu | Arg | Val | Leu | Tyr | Gly | Pro | Arg | Leu Asp Glu |
| 385 |     |     |     |     | 390 |     |     |     | 395 |     |     |     | 400 |
| AGG | GAT | TGT | CCG | GGA | AAC | TGG | ACG | TGG | CCA | GAA | AAT | TCC | CAG CAG ACT | 1248 |
| Arg | Asp | Cys | Pro | Gly | Asn | Trp | Thr | Trp | Pro | Glu | Asn | Ser | Gln Gln Thr |
|     |     |     |     | 405 |     |     |     | 410 |     |     |     | 415 |     |
| CCA | ATG | TGC | CAG | GCT | TGG | GGG | AAC | CCA | TTG | CCC | GAG | CTC | AAG TGT CTA | 1296 |
| Pro | Met | Cys | Gln | Ala | Trp | Gly | Asn | Pro | Leu | Pro | Glu | Leu | Lys Cys Leu |
|     |     |     | 420 |     |     |     | 425 |     |     |     | 430 |     |     |
| AAG | GAT | GGC | ACT | TTC | CCA | CTG | CCC | ATC | GGG | GAA | TCA | GTG | ACT GTC ACT | 1344 |
| Lys | Asp | Gly | Thr | Phe | Pro | Leu | Pro | Ile | Gly | Glu | Ser | Val | Thr Val Thr |
|     |     | 435 |     |     |     | 440 |     |     |     | 445 |     |     |     |
| CGA | GAT | CTT | GAG | GGC | ACC | TAC | CTC | TGT | CGG | GCC | AGG | AGC | ACT CAA GGG | 1392 |
| Arg | Asp | Leu | Glu | Gly | Thr | Tyr | Leu | Cys | Arg | Ala | Arg | Ser | Thr Gln Gly |
|     | 450 |     |     |     | 455 |     |     |     | 460 |     |     |     |     |
| GAG | GTC | ACC | CGC | GAG | GTG | ACC | GTG | AAT | GTG | CTC | TCC | CCC | CGG TAT GAG | 1440 |
| Glu | Val | Thr | Arg | Glu | Val | Thr | Val | Asn | Val | Leu | Ser | Pro | Arg Tyr Glu |
| 465 |     |     |     | 470 |     |     |     | 475 |     |     |     | 480 |     |
| ATT | GTC | ATC | ATC | ACT | GTG | GTA | GCA | GCC | GCA | GTC | ATA | ATG | GGC ACT GCA | 1488 |
| Ile | Val | Ile | Ile | Thr | Val | Val | Ala | Ala | Ala | Val | Ile | Met | Gly Thr Ala |
|     |     |     | 485 |     |     |     | 490 |     |     |     | 495 |     |     |
| GGC | CTC | AGC | ACG | TAC | CTC | TAT | AAC | CGC | CAG | CGG | AAG | ATC | AAG AAA TAC | 1536 |
| Gly | Leu | Ser | Thr | Tyr | Leu | Tyr | Asn | Arg | Gln | Arg | Lys | Ile | Lys Lys Tyr |
|     |     | 500 |     |     |     | 505 |     |     |     | 510 |     |     |     |
| AGA | CTA | CAA | CAG | GCC | CAA | AAA | GGG | ACC | CCC | ATG | AAA | CCG | AAC ACA CAA | 1584 |
| Arg | Leu | Gln | Gln | Ala | Gln | Lys | Gly | Thr | Pro | Met | Lys | Pro | Asn Thr Gln |
|     | 515 |     |     |     | 520 |     |     |     | 525 |     |     |     |     |
| GCC | ACG | CCT | CCC | TGA |     |     |     |     |     |     |     |     |     | 1599 |
| Ala | Thr | Pro | Pro |     |     |     |     |     |     |     |     |     |     |     |
| 530 |     |     |     |     |     |     |     |     |     |     |     |     |     |     |

(2) INFORMATION FOR SEQ ID NO:3:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ala Pro Ser Ser Pro Arg Pro Ala Leu Pro Ala Leu Leu Val Leu
 1               5                  10                  15

Leu Gly Ala Leu Phe Pro Gly Pro Gly Asn Ala Gln Thr Ser Val Ser
            20                  25                  30

Pro Ser Lys Val Ile Arg Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Pro Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
```

-continued

```
            130                 135                 140
Asn Leu Thr Val Val Leu Leu Arg Gly Glu Lys Glu Leu Lys Arg Glu
145                 150                 155                 160
Pro Ala Val Gly Glu Pro Ala Glu Val Thr Thr Val Leu Val Arg
            165                 170                 175
Arg Asp His His Gly Ala Asn Phe Ser Cys Arg Thr Glu Leu Asp Leu
            180                 185                 190
Arg Pro Gln Gly Leu Glu Leu Phe Glu Asn Thr Ser Ala Pro Tyr Gln
            195                 200                 205
Leu Gln Thr Phe Val Leu Pro Ala Thr Pro Gln Leu Val Ser Pro
210                 215                 220
Arg Val Leu Glu Val Asp Thr Gln Arg Thr Val Val Cys Ser Leu Asp
225                 230                 235                 240
Gly Leu Phe Pro Val Ser Glu Ala Gln Val His Leu Ala Leu Gly Asp
            245                 250                 255
Gln Arg Leu Asn Pro Thr Val Thr Tyr Gly Asn Asp Ser Phe Ser Ala
            260                 265                 270
Lys Ala Ser Val Ser Val Thr Ala Glu Asp Glu Gly Thr Gln Arg Leu
            275                 280                 285
Thr Cys Ala Val Ile Leu Gly Asn Gln Ser Gln Glu Thr Leu Gln Thr
            290                 295                 300
Val Thr Ile Tyr Ser Phe Pro Ala Pro Asn Val Ile Leu Thr Lys Pro
305                 310                 315                 320
Glu Val Ser Glu Arg Thr Glu Val Thr Val Lys Cys Glu Ala His Pro
            325                 330                 335
Arg Ala Lys Val Thr Leu Asn Gly Val Pro Ala Gln Pro Leu Gly Pro
            340                 345                 350
Arg Ala Gln Leu Leu Leu Lys Ala Thr Pro Glu Asp Asn Gly Arg Ser
            355                 360                 365
Phe Ser Cys Ser Ala Thr Leu Glu Val Ala Gly Gln Leu Ile His Lys
            370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
            405                 410                 415
Pro Met Cys Gln Ala Trp Gly Asn Pro Leu Pro Glu Leu Lys Cys Leu
            420                 425                 430
Lys Asp Gly Thr Phe Pro Leu Pro Ile Gly Glu Ser Val Thr Val Thr
            435                 440                 445
Arg Asp Leu Glu Gly Thr Tyr Leu Cys Arg Ala Arg Ser Thr Gln Gly
            450                 455                 460
Glu Val Thr Arg Glu Val Thr Val Asn Val Leu Ser Pro Arg Tyr Glu
465                 470                 475                 480
Ile Val Ile Ile Thr Val Val Ala Ala Ala Val Ile Met Gly Thr Ala
            485                 490                 495
Gly Leu Ser Thr Tyr Leu Tyr Asn Arg Gln Arg Lys Ile Lys Lys Tyr
            500                 505                 510
Arg Leu Gln Gln Ala Gln Lys Gly Thr Pro Met Lys Pro Asn Thr Gln
            515                 520                 525
Ala Thr Pro Pro
530
```

(2) INFORMATION FOR SEQ ID NO:4:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GATTGAAGAA GCCAGCAG                                                       18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTCGTTGCCA TAGGTGAC                                                       18

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCCCTGGACG GGCTGTTCC                                                      19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCCCTGGACA GGCTGTTCC                                                      19
```